United States Patent [19]
Lewis et al.

[11] Patent Number: 6,072,167
[45] Date of Patent: Jun. 6, 2000

[54] ENHANCED UNIFORMITY IN A LENGTH INDEPENDENT MICROWAVE APPLICATOR

[75] Inventors: David Andrew Lewis, Carmel; Stanley Joseph Whitehair, Peekskill, both of N.Y.

[73] Assignee: International Business Machines Corporation, Armonk, N.Y.

[21] Appl. No.: 09/002,849

[22] Filed: Jan. 5, 1998

Related U.S. Application Data

[60] Provisional application No. 60/034,718, Jan. 6, 1997.

[51] Int. Cl.$^7$ ........................................ H05B 6/70
[52] U.S. Cl. ..................... 219/690; 219/691; 219/693; 219/696; 219/698; 219/750
[58] Field of Search ..................... 219/690–701, 219/702, 715, 745, 746, 750, 752, 753

[56] References Cited

U.S. PATENT DOCUMENTS

| | | | |
|---|---|---|---|
| 3,461,261 | 8/1969 | Lewis et al. | 219/690 |
| 3,739,130 | 6/1973 | White | 219/696 |
| 3,784,777 | 1/1974 | Soulier | 219/690 |
| 5,241,040 | 8/1993 | Cuomo et al. | 528/353 |
| 5,250,773 | 10/1993 | Lind et al. | 219/696 |
| 5,471,037 | 11/1995 | Goethel et al. | 219/750 |

*Primary Examiner*—Tu Ba Hoang
*Attorney, Agent, or Firm*—Thomas A. Beck

[57] ABSTRACT

A microwave applicator including a cylindrical elongated chamber used to process materials therein; a microwave power source capable of producing microwave power having an electric field; a waveguide connected to the chamber couples microwave power into the microwave chamber. The applicator provides microwave energy having a substantially uniform field distribution over a large area for processing materials such as a web or sheet-like product. The uniformity of the applicator is enhanced by the use of matching devices within the applicator to match the regions of the applicator with no load to regions where the load is present in a continuous manner.

21 Claims, 4 Drawing Sheets

FIG.3B
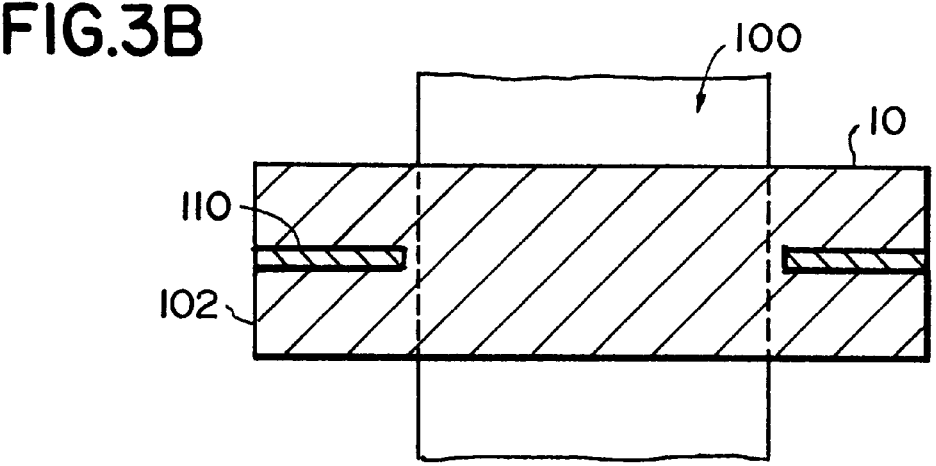
FIG.3C
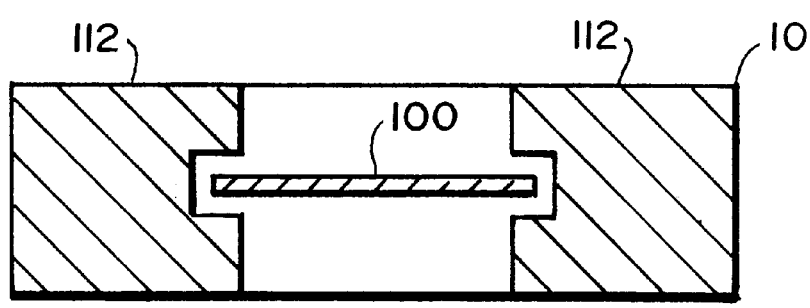
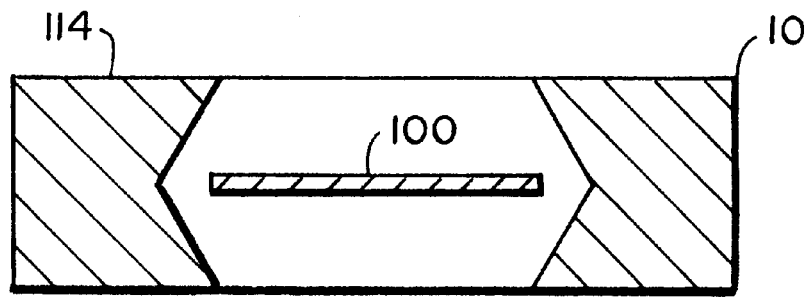
FIG.3D

ENHANCED UNIFORMITY IN A LENGTH INDEPENDENT MICROWAVE APPLICATOR

This application claims the priority from U.S. Provisional Application Ser. No. 60/034,718 filed Jan. 6, 1997.

FIELD OF INVENTION

The present invention is related to microwave applicators and, more particularly, to a means to enhance the uniformity of an electric field pattern in a single mode microwave applicator.

BACKGROUND OF THE INVENTION

Microwave radiation can be applied to a material in a number of ways, using single mode applicators, multimode applicators, traveling wave applicators, slow wave applicators, fringing field applicators and through free space. Each of the aforementioned methods of coupling microwave energy into a material has its advantages and disadvantages which usually depend on the dielectric properties, size and shape, of the materials to be processed and the type of processing (batch, continuous, liquid, plasma, etc) to be performed.

Efficient microwave energy transfer is a function of many variables as processing occurs. A number of these variables are material related, e.g., the material type and density and material temperature as well as the time history of both the material temperature and the applied electric field.

Other factors that influence coupling are related to the applicator, material geometry and size and the frequency or wavelength of the electromagnetic energy. Electromagnetic coupling depends on applicator size and geometry, material size and shape, the position of the material within the applicator, and even the relative sizes and shapes of the material and the applicator. In addition, both the applicator and material dimensions may change during heating which further complicates the efficient transfer of energy to the material.

Accordingly, a problem arises when attempting to generate a uniform microwave field across a relatively large surface for different material loads. As generally understood, if the volume of an applicator becomes too large, more than one electric field pattern can co-exist in the applicator, thereby making it multimode and introducing electric field non-uniformities. Current microwave applicators are incapable of generating a uniform microwave field across a surface that is relatively large compared to the wavelength of the radiation.

For instance, traveling wave applicators have some potential for providing uniformity. However, stray reflections, such as those that occur at the edges of a workpiece or any non-uniformity in the structure of the applicator can create standing waves leading to thermal non-uniformities. This is especially problematic in cases in which the material travels through more than one applicator and the dielectric properties of the material change depending on the processing conditions in the previous applicator.

An applicator design which shows some promise for applying uniform fields is a single mode applicator, provided that the fields can be extended over a sufficiently large region. This type of applicator can be tuned to specific electric field patterns (resonance modes) by varying the volume of the applicator.

One such approach is found in U.S. Pat. Nos. 4,507,588, 4,585,668, 4,630,566, 4,727,293, and 4,792,772 (Asmussen) all of which disclose methods and apparatuses in which a single mode resonant microwave applicator can be critically coupled by varying two separate, almost orthogonal variables, specifically the cavity length (by moving a short circuit) and the antenna position.

The Asmussen devices include a variable penetration antenna structure which acts to launch radiation into the applicator. The main advantage of the Asmussen device is that it enables complete critical coupling over a wide range of impedances (generated by the load in the applicator) and without the use of any external coupling structure. Critical coupling can thus be achieved by moving the short and the antenna appropriately.

By moving the flat part of the cavity wall (in a cylinder) in the z-direction (e.g., along the centerline of the cylinder), a wide range of electromagnetic modes can be established and maintained, even as the load varies (due to processing, e.g., temperature changing, material curing, etc.) However, one series of modes that can not be routinely excited are length independent modes, $TM_{xy0}$. The resonant frequency of these modes are only dependent on the diameter of the loaded structure. As a result, if the load changes during processing (e.g., the dielectric properties change, due to increased temperature, curing, phase change in the material and so forth), the resonant frequency in the cavity changes from an initial, fixed processing frequency, usually 2450 MHz or 915 MHz (which are the ISM bands allowed by the Federal Communication Commission (FCC)). The Asmussen devices are thus not capable of maintaining certain modes in a controlled manner, namely the length independent modes ($TM_{xy0}$) because these modes are dependent on the diameter of the applicator only.

In general, to process wide objects in a continuous manner, such as a web or sheet like product, as found in the paper industry, lumber industry (plywood) or electronics industry (in pre-impregnated cloth for circuit board manufacture), it is desirable to be able to (i) provide a uniform electric field over the entire product for uniform heating; (ii) vary the applicator to allow for variations in the dielectric properties of a continuously moving workpiece and, thus, vary the coupling of the radiation to the product; and (iii) control the microwave power reaching the product to control the temperature-time profile of the web.

The electric field pattern sustained by the $TM_{0y0}$ series of modes, where y=1, 2 or greater, is oriented along the z-axis of the applicator and is of constant intensity along the entire length of the applicator for an empty cavity. This is an ideal mode for the processing of a web-like material. Referring to FIG. 1 (a mode chart), it can be seen that the $TM_{010}$ mode is independent of the cavity length. Therefore, a low loss, infinitely long applicator is capable of sustaining the same electric field intensity throughout the length.

However, the electric filed is only truely uniform if the dielectric material uniformly fills the entire length of the applicator (ie, the material to be processed is as wide as the microwave applicator is long and has the same thickness along its width). If this condition is not met, and some means used to correct the situation, the electric field will cease to become uniform at the edges of the workpiece and potentially for up to a significant distance into the workpiece. This occurs for 2 reasons, first, the discontinuity creates a evanescent field, and second, the discontinuity changes the resonant condition of the cavity.

Evanescent fields occur at all discontinuities, however, through careful design and setup they can be minimized. The largest evanescent fields occur at sharp boundaries with large variations in dielectric constant and the electric field vector in the direction normal to the boundary. To minimize this field we avoid these conditions as much as possible. This includes avoid sharp boundaries and avoiding boundaries where the electric field is normal to the surface. In addition, dielectric structures can be added that help to minimize the evanescent fields by minimizing the boundary condition. Usually, these matching structures match the boundary condition of the origional structure in such a manner as to cancle the origional evanescent field.

Discontinuties also affect the resonant condition of the cavity. This occurs since the resonant frequency of the applicator in the regions where no workpiece (load) is present is different from that of the region where the workpiece is present. If the resonant frequencies of these regions is similar enough (by the workpiece providing a relatively small load on the applicator) relatively efficient coupling between the regions can be maintained and hence a relatively uniform electric field strength across the workpiece is maintained. If there is a sufficient difference in the resonant frequencies of the regions, the difference in resonant frequencies is greater than the bandwidth of the regions (which is due to losses and can be measured by a network, typically using the frequency width of the resonance at half power)and minimal power is coupled between the regions and hence the edge of the workpiece acts as an impedance mismatch, resulting in a non-uniformity in the heating of the workpiece.

Accordingly, it is an object of the present invention to provide a means of effectively enhancing the uniformity of the microwave energy over the full width of the workpiece by effectively minimizing the impedance mismatch at the adges of a workpiece and providing improved energy field distribution over a wide area, as compared to the prior art.

It is also an object of the invention to provide an elongated cylindrical microwave applicator that allows a uniform electric and magnetic field to be applied to a sheet of material being transported therethrough, in a continuous manner.

It is a further object of the invention to provide an elongated cylindrical microwave applicator that launches radiation at more than one input and provides uniform electric and magnetic fields along its length.

SUMMARY OF THE INVENTION

A microwave applicator includes an elongated chamber, preferably having a cylindrical shape, for processing materials therein. A waveguide, connected to the elongated chamber, couples microwave power into the elongated chamber. The applicator thus provides microwave energy having a substantially uniform field distribution over a large area for processing materials, for example, a web in a continuous manner.

One embodiment provides a structure in which an appropriate material is inserted into the regions of the applicator where no workpiece is present to cause the electric field to be more uniform.

Another embodiment provides a means of reducing the diameter of the appicator in the region of the workpiece in order to maintain an effective impedance match between the regions of the applicator containing the workpiece and region not, thereby providing an enhanced uniformity of microwave energy across the workpiece.

DETAILED DESCRIPTION OF THE INVENTION

Figure 1:
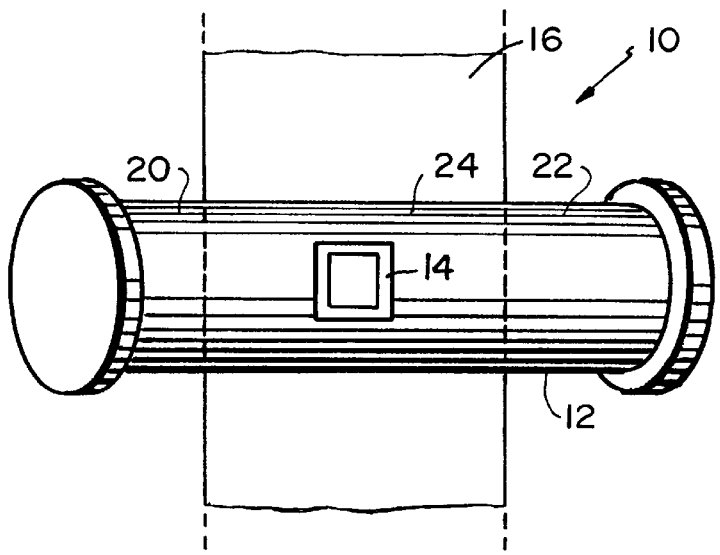
FIG. 1 illustrates the regions in a cylindrical microwave applicator containing the workpiece and indicates the regions with and without a workpiece.

Referring to FIG. 1, a microwave applicator 10 in accordance with the present invention includes an elongated cylindrical chamber 12 acting as a resonant cavity therein fabricated from 2 half cylinders, with a space between the half cylinders. A power source is coupled to the resonant cavity preferably through a flange end waveguide extension 14. The energy is launched into cylindrical chamber 12, via waveguide extension 14. Note that, depending on the type of load or processing, the energy can be end launched from one end of the cylinder, side launched through a side wall of the cylinder or multi-launched.

The design of applicator 10 is useful for processing web-like materials 16. Such materials may be inserted into applicator 10 through a space provided between first and second cylindrical halves (i.e., the web moves orthogonally to the plane of the drawing).

The cylindrical chamber 12 may be an aluminum tube having a thickness of approximately 0.250 inches and a length of approximately 19.750 inches.

In the operation of the invention, when a material load 16 is placed in the empty resonant cavity of the applicator 10, each electromagnetic resonance in the region of the material 24 is shifted down in frequency and Q is lowered compared to regions 20 and 22, where no material is present. The presence of the material load adds an additional material conductance and susceptance to the circuit. These additional circuit elements are functions of the material load placement, volume, shape and material properties.

Figure 2:
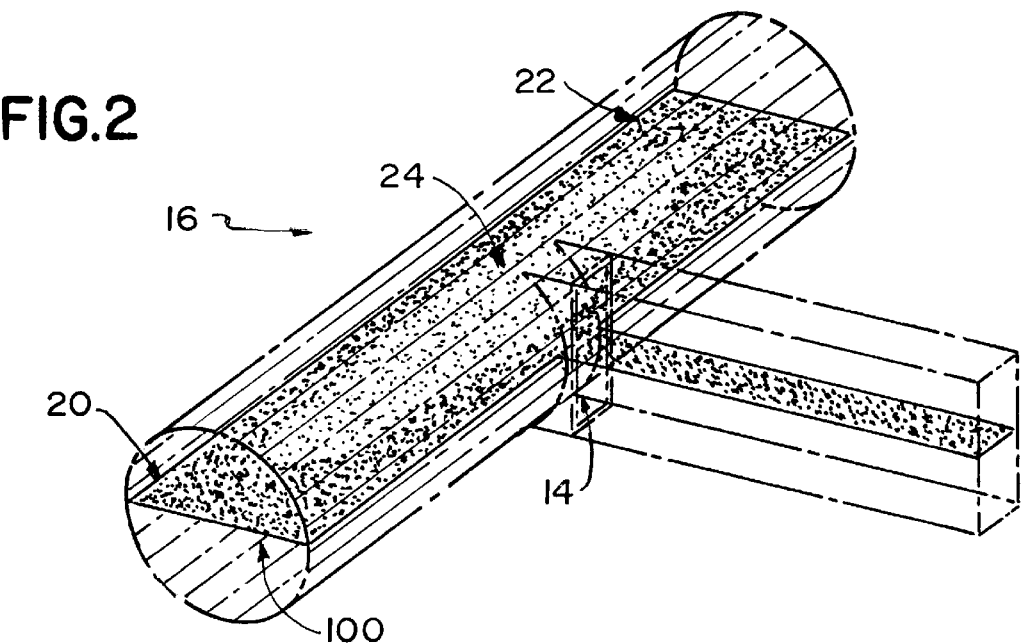
FIG. 2 illustrates an electric field pattern obtained from a finite element analysis indicating the relative electric field strength over the width of the applicator and showing the non-uniformity of the electric field pattern over the region of the workpiece.

As shown in FIG. 2, there is a substantial non-uniformity in the electric field at the boundary of the workpiece, as seen by the discontinuity of the electric field strengths and by the rapid decrease in the electric field strength in that region.

Figure 3A:
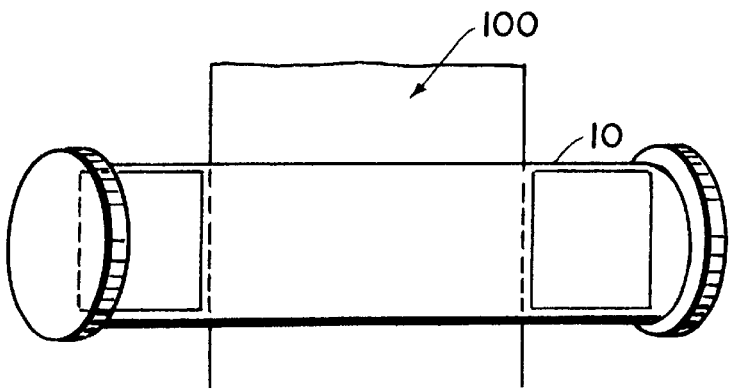
FIG. 3 illustrates the shape and positions of dielectric plates (a) parallel to the workpiece; (b) perpendicular to the workpiece; (c) a different view showing the positioning perpendicular to the workpiece; (d) an irregular shaped dielectric plate placed perpendicular to the workpiece; (e) plates arranged parallel to but in a different plane of the workpiece.

In accordance with the first object of the current invention, dielectric plates can be inserted into the microwave applicator in regions 20 and 22 to provide an impedance match between region 24 and regions 20 and 22. These plates can be orietented parallel or perpendicular to the workpiece direction and can come very close, but not in contact with the workpiece (to prevent deposition of material from the workpiece onto the plates, thereby compromizing long useage of the plates). This can be seen in FIG. 3(a) which shows a side view of the workpiece 100 in the applicator 10 and showing the dielectric plate 110 coming close to, but not in contact with the workpiece 100 and oriented perpendicular to the workpiece 100. In this figure, the dielectric plate 110 is shown filling the entire space from the workpiece to the endplate of the applicator 102. FIG. 3(b) shows a plan view of the dielectric plate 112 which is oriented parallel to the workpiece 100 in the applicator 10. FIG. 3(c) shows a plan view of the applicator 10 in which the shape of the dielectric plate 114 extends past the workpiece 100 with a notch immediately in the region of the workpiece, to ensure a smooth transition in the impedance across the junction of the workpiece and the edge of the dielectric plate. This is further improved in FIG. 3(d) which shows a gradual transition of the dielectric plate in the region of the edge of the workpiece.

Figure 3E:
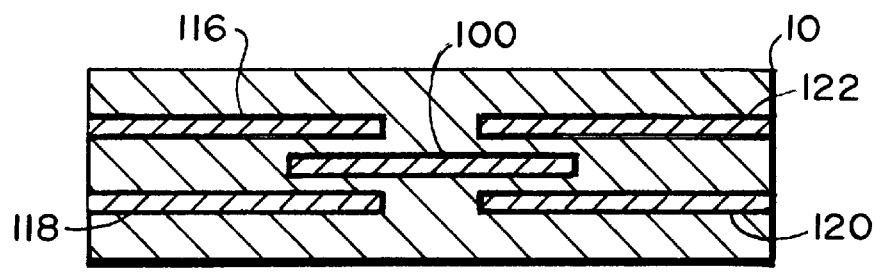

It should be realized that the electric field is maximum in the region in the exact center of the applicator 10. Hence, it is preferable to place the workpiece 10 passing through this region to maximise the energy deposition into the workpiece. This also causes the maximum perturbation in the electric field and hence the maximum change in the impedance, thereby providing the maximum difference in passing from the workpiece region 24 to an empty region 20 or 22 of the applicator. Therefore, by placing the dielectric plate such that it is coincident with the center axis of the applicator, the mass of dielectric used to form the dielectric plates can be minimized. However, this is not necessary, as shown in FIG. 3(e) which shows a plan view of an applicator 10 with a workpiece 100 and two pair of dielectric plates, 116, 118, 120 and 122 providing a means to exactly make the edges of the dielectric plates and the workpiece coincide without risk of contact between the workpiece and the dielectric plates. In a similar manner, as the edges of the dielectric plate 124 in FIG. 3(d) move from the center axis of the applicator 10, the influence and effectiveness of the dielectric plate diminishes rapidly (according to the bessel function for the mode being excited in the applicator) thereby providing a gradual impedance match.

FIG. 2 shows the electric field strength over the cross-section of the microwave applicator 10 in which the workpiece 100 (with a dielectric constant of 30 and thickness of 0.1 mm) is in position, but with no dielectric plate present. A non-uniformity in the electric field is noted in two ways—a discontinuity at the edge of the workpiece and in the manner in which the field is decreasing in the region approaching the edge of the workpiece 100. These non-uniformities in the electric filed will result in undesirable non-uniformities in the heating of the workpiece.

Figure 4:
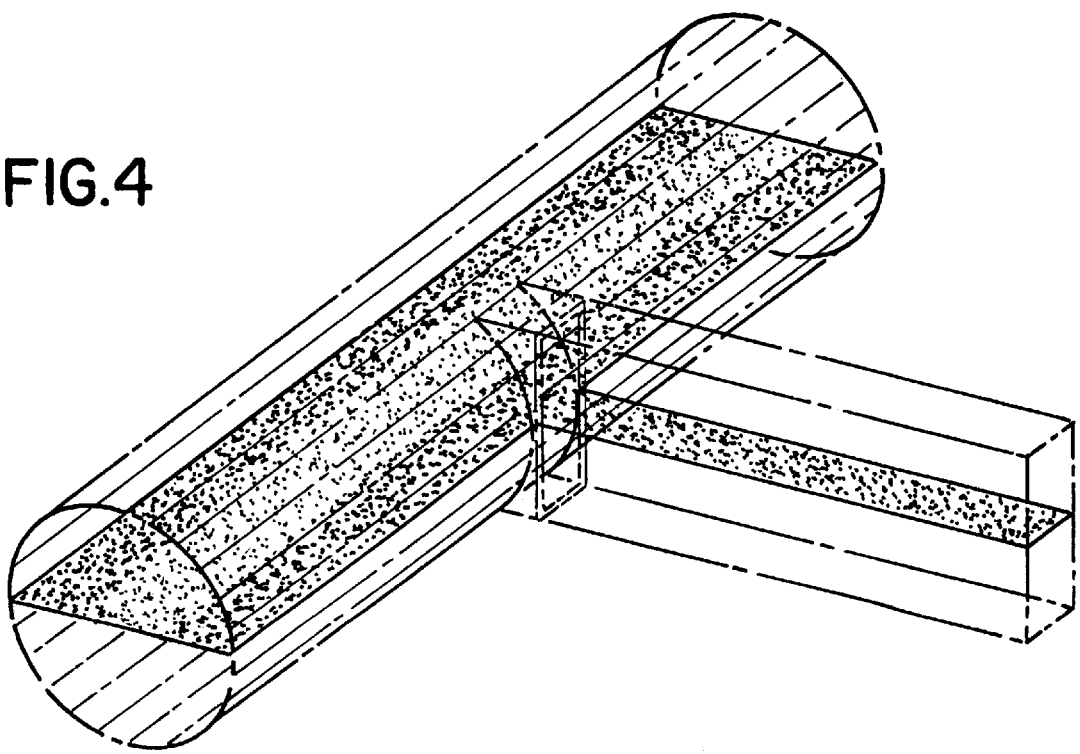
FIG. 4 illustrates an electric field pattern obtained from a finite element analysis indicating the relative electric field strength over the width of the applicator constructed in accordance with the present invention with a minimal dielectric insert in the region adjacent to the workpiece and showing the non-uniformity of the electric field pattern over the region of the workpiece.

If a dielectric plate of thickncess 1 mm and a dielectric constant of 3 is placed according to FIG. 3(a), the electric field pattern as shown in FIG. 4 is substantially improved.

Figure 5:
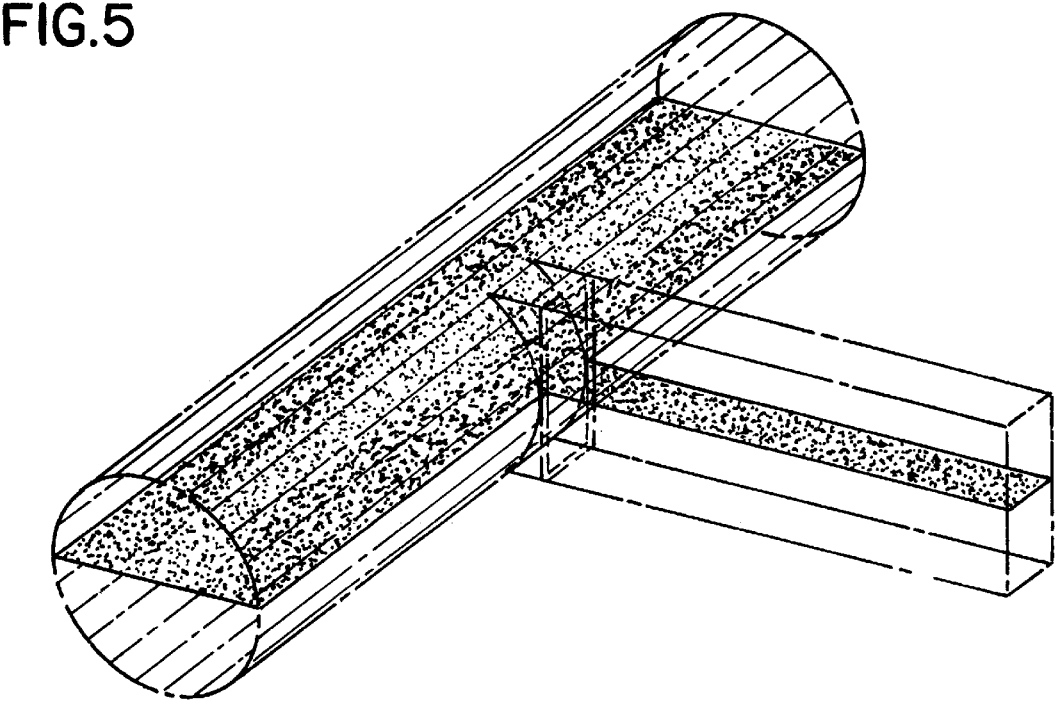
FIG. 5 illustrates an electric field pattern obtained from a finite element analysis indicating the relative electric field strength over the width of the applicator constructed in accordance with the present invention with a satisfactory dielectric insert in region ?? and showing the uniformity of the electric field pattern over the region of the workpiece that can be obtained.

It has been discovered that it is desirable for the dielectric load (dielectric constant multiplied by thickness) of the dielectric plates to be greater than that of the workpiece. By increasing the dielectric constant of the dielectric plate further to 5, as shown in FIG. 5, the electric field is substantially uniform across the entire applicator, and in particular across the workpiece, resulting in excellent uniformity of heating in the workpiece. This also indicates that it is not necessary to perfectly match the dielectric load of the workpiece to that of the dielectric plates and it is only necessary to ensure that the dielectric load of the plates is comparable or greater than that of the workpiece.

It should be noted that the electric field properties in this applicator are symetric, such that each edge of the workpiece behaves in a similar manner and hence the placement and positioning of the dielectric plates will be optimal if they are placed in a symetric configuration.

The dielectric plates can be made to be interachangable, such that if the properties of the workpiece were to change substantially, different dielectric plates could be installed.

Figure 6:
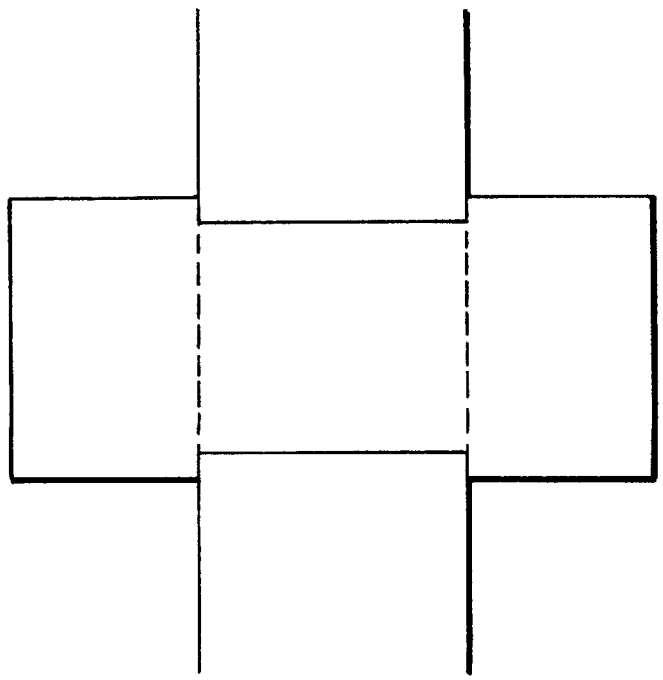
FIG. 6 illustrates a side schematic view of a microwave applicator constructed in accordance with the second embodiment of the present invention.

In a second embodiement of this invention, the resonant frequency of the region 24 containing the workpiece 16 and and regions 20 and 22 in which there is no workpiece, can be matched by varying the diameter of the applicator in region 24 with respect to regions 20 and 22 as shown in FIG. 6. Since region 24 has the largest dielectric load in the applicator 10, this region will have the lowest resonant frequency and hence require the smaller diameter (compared to regions 20 and 22). By placing a metallic sleeve into the applicator 10 in the region 24, a smaller radius will be obtained. Conversely, regions 20 and 22 could be machined to remove material and thereby increase the diameter of the applicator in thos regions. The disadvantage of this approach is that the modifications are permanent and will be optimized for only one dielectric load (ie thickness and dielectric constant). If the dielectric load were to change, the applicator would have to be replaced with modificatios to the radius to match the new dielectric material to be processed. Furthermore, there is now a discontinuity in the walls in the regions between 24 and 20 and 22.

Microwave radiation can be coupled into applicator 10 using an iris, loop or antenna placed on the outer surface of the applicator or from the end of the applicator (e.g., end launch). The choice between the aforementioned devices depends on the material to be processed, the manner in which the dielectric properties change during processing and the resonant mode being utilized. Multiple launchers can also be used to improve uniformity and to generate higher power levels in the cavity.

When the iris is placed on the outer wall of the applicator 10 and the fundamental mode of the launch waveguide is utilized, the length independent $TM_{0n0}$ modes are preferably selected. However, whenever there is a load in applicator 10 this provides a means for mode switching to other modes if the resonant frequency for that mode matches the microwave frequency. This problem is exacerbated as the length of the applicator is increased substantially since the normally length dependent modes can now be selected or sustained.

The invention having thus been described with particular reference to the preferred forms thereof, it will be obvious that various changes and modifications may be made therein without departing from the spirit and scope of the invention as defined in the appended claims.

We claim:

1. An apparatus for applying microwave energy having a substantially uniform field distribution over a large area for processing a material comprising:

an elongated cylinder chamber;

a workpiece contained within said elongated cylinder chamber;

a microwave power source capable of producing microwave power having an electric field pattern;

means for coupling said microwave power into said elongated cylinder chamber;

and a dielectric matchpiece having a predetermined shape, said matchpiece being substantially transparent to microwaves positioned in said elongated cylinder chamber in a predetermined position and capable of modifying said electric field pattern said dielectric matchpiece providing enhanced uniformity of heating in said workpiece.

2. An apparatus as recited in claim 1, wherein said elongated chamber is separated into two halves along a length of said elongated cylinder chamber.

3. An apparatus as recited in claim 1 in which the dielectric matchpiece is fabricated from a low loss material.

4. An apparatus as recited in claim 2, wherein said elongated chamber includes a space between and along the length of said two halves for allowing a sheet of material to pass therethrough.

5. An apparatus as recited in claim 1, wherein said elongated chamber operates in a length independent mode.

6. An apparatus as recited in claim 1, wherein said elongated chamber operates in a $TM_{0r0}$ mode.

7. An apparatus as recited in claim 1, wherein microwave energy having a substantially uniform electric field pattern is applied across the length of said elongated cylinder chamber.

8. An apparatus as recited in claim 1, wherein said elongated chamber includes an entrance opening and exit opening for allowing a sheet of material to pass through a center region of said elongated chamber.

9. An apparatus as recited in claim 1, wherein said large area extends substantially over the width of a sheet of material passing through said elongated chamber.

10. An apparatus as recited in claim 1, wherein said elongated chamber has an approximately circular cross-section.

11. An apparatus as recited in claim 1 in which the dielectric matchpiece is a plate.

12. An apparatus as recited in claim 1 in which the dielectric matchpiece is a cylinder.

13. An apparatus for applying microwave energy having a substantially uniform field distribution over a large area for processing a material comprising:

an elongated cylinder chamber;

a workpiece contained within said elongated cylinder chamber;

said elongated cylinder chamber acting as a resonant cavity and fabricated from two half-cylinders with a space between said half cylinders, a microwave power source capable of producing microwave power having an electric field;

means for coupling said microwave power into said elongated cylinder chamber;

said elongated cylinder chamber containing a web of predetermined width inserted therein through said space between said half cylinders for modifying said electric field and providing enhanced uniformity of heating in said workpiece; and variation in diameter of said elongated cylinder chamber exactly matching width of web.

14. An apparatus as recited in claim 13, wherwin said elongated chamber is separated into two halves along a length of said elongated chamber.

15. An apparatus as recited in claim 13, wherein said elongated chamber includes a space between and along the length of said two halves for allowing a sheet of material to pass therethrough.

16. An apparatus as recited in claim 13, wherein said elongated chamber operates in a length independent mode.

17. An apparatus as recited in claim 13, wherein said elongated chamber operates in a $TM_{0r0}$ mode.

18. An apparatus as recited in claim 13, wherein microwave energy having a substantially uniform electric field pattern is applied across the length of said elongated chamber.

19. An apparatus as recited in claim 13, wherein said elongated chamber includes an entrance opening and exit opening for allowing a sheet of material to pass through a center region of said elongated chamber.

20. An apparatus as recited in claim 1, wherein said elongated chamber has an approximately square cross-section.

21. An apparatus as recited in claim 1, wherein said elongated chamber has an approximately rectangular cross-section.

* * * * *